United States Patent [19]

Sugihara et al.

[11] Patent Number: 5,048,336

[45] Date of Patent: Sep. 17, 1991

[54] MOISTURE-SENSITIVE DEVICE

[75] Inventors: Takashi Sugihara, Ryugasaki; Kazutaka Uda; Hiroki Tabuchi, both of Nara; Shuji Miyoshi, Yamatokouriyama; Yasuhiko Inami; Nobuo Hashizume, both of Nara; Hisatoshi Furubayashi, Yamatokouriyama, all of Japan

[73] Assignee: Sharp Kabushiki Kaisha, Osaka, Japan

[21] Appl. No.: 459,262

[22] Filed: Dec. 29, 1989

[30] Foreign Application Priority Data

Dec. 29, 1988 [JP] Japan .................. 63-332348
Sep. 5, 1989 [JP] Japan .................. 1-229873

[51] Int. Cl.⁵ ............................. G01N 27/12
[52] U.S. Cl. .................. 73/336.5; 73/29.05; 338/35
[58] Field of Search ............ 73/336.5, 29.05; 338/35

[56] References Cited

U.S. PATENT DOCUMENTS

| | | | |
|---|---|---|---|
| 4,419,888 | 12/1983 | Kitamura et al. | 73/336.5 |
| 4,562,725 | 1/1986 | Oka et al. | 73/29.05 |
| 4,723,439 | 2/1988 | Asakura et al. | |
| 4,740,387 | 4/1988 | Manaka | |
| 4,928,513 | 5/1990 | Sugihara et al. | 338/35 X |

FOREIGN PATENT DOCUMENTS

| | | |
|---|---|---|
| 0265834 | 5/1988 | European Pat. Off. |
| 3724966 | 2/1988 | Fed. Rep. of Germany |
| 55-181537 | 12/1980 | Japan |
| 61-201148 | 9/1986 | Japan |
| 63-145954 | 6/1988 | Japan |
| 63-201559 | 8/1988 | Japan |
| 201561 | 8/1988 | Japan .................. 73/336.5 |
| 63-243817 | 10/1988 | Japan |
| 63-263426 | 10/1988 | Japan |
| 2172999 | 10/1986 | United Kingdom ......... 73/336.5 |

OTHER PUBLICATIONS

Copy of European Search Report.
K. Uda et al., "Micro-Bridge Type Absolute Humidity Sensor", *The 9th Chemical Sensor Symposium*, Aoyama Gakuin University, Oct. 21-22, 1989.

*Primary Examiner*—Herzon E. Williams
*Assistant Examiner*—Joseph W. Roskos
*Attorney, Agent, or Firm*—Sandler, Greenblum & Bernstein

[57] ABSTRACT

A moisture-sensitive device comprising a substrate such as silicon substrate, a pair of belt-like heating elements extending over recesses formed in the substrate, the heating elements being composed of a resistive film of platinum or nickel and a heat-resistant insulating film covering the resistive film in which one of the heating elements acts as a detector element and the other as a reference element, which device can exactly determine an absolute humidity irrespective of sudden changes of temperature.

11 Claims, 11 Drawing Sheets

MOISTURE-SENSITIVE DEVICE

BACKGROUND OF THE INVENTION

1. Field of the Invention

The present invention relates to a moisture-sensitive device and, more particularly, to a moisture-sensitive device which has a detector element and a reference element and which determines the absolute humidity from the difference between the outputs from these two elements.

2. Description of the Prior Art

Various kinds of humidity sensors have been heretofore developed. Some of them detect relative humidities of the atmosphere, while the others detect absolute humidities. Humidity sensors which detect relative humidities are superior with respect to certain factors, such as detection range, sensitivity, accuracy, response speed, reliability, and environmental resistance, but inferior in the other factors. Where such a humidity sensor is placed within a microwave oven that is being operated, the temperature of the atmosphere surrounding the sensor changes rapidly. Under these conditions, when very slight changes in the amount of water vapor are detected, the relative humidity that is a function of temperature is considered as follows.

It is assumed that the amount of water vapor contained in the detected atmosphere is constant and that only the temperature of the atmosphere increases. Event if the amount of water vapor is constant, the relative humidity drops because the saturated water vapor pressure changes. If temperature is elevated at a higher rate, then a very slight increase in the amount of water vapor will not change the relative humidity because of the increase in temperature, or it might lead to a decrease in the relative humidity. Consequently, the result obtained does not substantially change in the amount of water vapor. In this way, this kind of humidity sensor has a serious problem. Hence, a sensor which can directly detect the amount of water vapor is better adapted to measure the humidity of the aforementioned environment, rather than a sensor detecting the relative humidity.

In order to detect absolute humidities or the amount of water vapor, instruments making use of attenuation of microwaves due to water vapor or absorption of infrared radiation have been employed. Since these instruments can directly detect the amount of water vapor by physical means, they are adapted for detection of slight changes in the amount of water vapor even in an environment involving a rapid temperature change as described above. However, these instruments which includes means for providing temperature compensation are large-scale and considerably expensive to fabricate.

Figure 9:
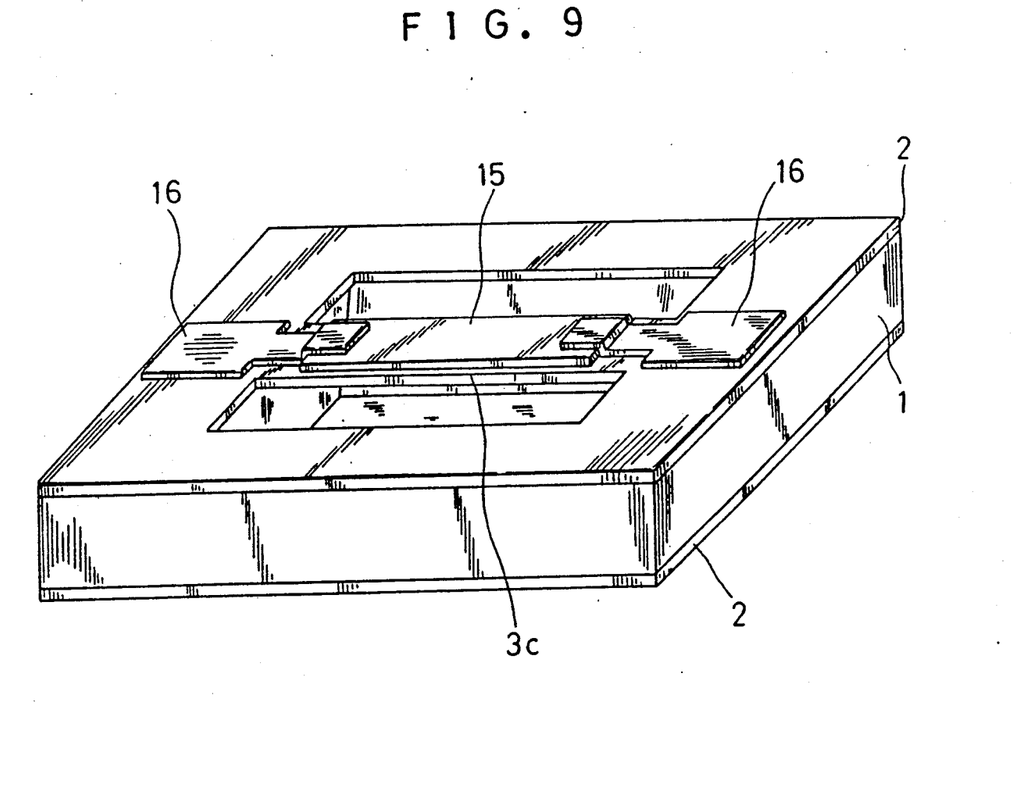
FIG. 9 is a perspective view of a micro bridge type element using a prior art thermistor thin film.

In view of the foregoing, the present applicant and others have developed various small-sized absolute humidity sensors which are excellent in environmental resistance and weatherproofness, and are fabricated using micromachining techniques, as disclosed in Japanese Patent Laid-Open Nos. 145,954/1988, 201,559/1988, 243,817/1988, and 263,426/1988. A typical absolute humidity sensor is shown in FIG. 9, where insulating layers 2 are formed on the surface of a substrate 1. A bridge 3c made of an insulating thin film is formed over one insulating layer 2. A heating element 15 made of a thin film of a thermistor material is formed on the bridge 3c. The heat capacity of this device is very small. The insulating thin film can assume the form of a cantilever or a diaphragm, as well as the form of a bridge. The thermistor material can be SiC, TaN, Ge, or other material. An absolute humidity sensor using a thin-film heating element made from such a thermistor material shows high response speed and high sensitivity,, but the thin film is not stable over a long period of time. In particular, it is not stable against heat. Further, the device is not easy to manufacture, because it is necessary to form electrodes 16, and for other reasons. In a proposed structure of the absolute humidity sensor using a thermistor material as described above, a detector element and a reference element are formed on a single substrate to provide temperature compensation. The reference element is hermetically sealed. However, this humidity sensor also suffers from the above-described drawbacks, since it uses a thermistor material.

As a kind of temperature sensor, a flow sensor using a heating element made of a thin film of platinum is known. The heating element of this sensor is shaped like a bridge in the same way as the device described in connection with FIG. 9. This flow sensor can operate from room temperature to 50° C. or below. The heating element is exposed to the surrounding environment so that it may be directly subjected to flow of the environment.

SUMMARY OF THE INVENTION

It is an object of the present invention to provide a moisture-sensitive device which is free of the foregoing problems characteristic of prior art techniques.

The above object is achieved by a moisture-sensitive device comprising: a substrate provided with a pair of recesses; a pair of belt-like heating elements extending over the recesses and formed on the same side as, or opposite side of, the openings of the recesses; an insulator formed between the substrate and the heating elements; a container the inside of which is an atmosphere of a given humidity, the container being formed integral with the substrate and acting to isolate one of the heating elements from the outside atmosphere; lead wires for supplying electric current to the heating elements; and the heating element being a resistive film of platinum or nickel and a heat resistant insulating film covering the resistive film.

The moisture-sensitive device detects absolute humidities by making use of the fact that the thermal conductivity of air depends on the amount of water vapor contained in air.

DESCRIPTION OF THE PREFERRED EMBODIMENTS

A moisture-sensitive device according to the invention includes a substrate which is provided with at least one pair of recesses. These recesses are shaped so as to, contribute to a reduction in the heat capacity of the finished moisture-sensitive device, and also to provide sufficient heat insulation from the belt-like heating elements (described later). Preferably, the recesses are shaped into substantially the same form. The low heat capacity and the heat insulation from the belt like heating elements are of importance for the reasons described below.

Generally, it is necessary to increase the amount of heat dissipated from a device as much as possible for a given change in the amount of water vapor, in order to enhance the sensitivity of the device. The amount of heat dissipated from the device is given by the equation $$q = h(T - T_0)A$$

where T is the temperature (° C.) of the device, A is the area (m$^2$) of the surface of the device, h is the heat transfer coefficient (kcal/m.h.° C.), and $T_0$ is the temperature (° C.) of the atmosphere. The amount of dissipated heat q is represented in kcal/h. When the amount of water vapor changes, only the heat transfer coefficient h varies; A is retained constant, since it is the area of the surface. Accordingly, for a certain change in the amount of water vapor, the amount of heat dissipated q can be increased by increasing $(T - T_0)$, i.e., elevating the temperature T of the device. However, if the measures taken are only to increase the operating temperature of the device, then the amount of electric power consumed by the device increases greatly. This leads to a great decrease in the speed of response of the device to heat, which will result in a substantial reduction in the speed of response to water vapor. Therefore, it is important to reduce the heat capacity of the device, i.e., to provide sufficient heat insulation from the heating elements of the device, to achieve high-speed response, low power consumption, and high-temperature operation.

The novel moisture-sensitive device of the invention is equipped with a pair of belt-like heating elements, corresponding to the above-described recesses. Specifically, the heating elements are supported on the substrate via an insulator and disposed close to the opening of the recesses, or the heating elements are disposed via a insulator on the surface of the substrate which is on the opposite side of the recesses. In the former case, the elements can be supported by a bridge-shaped, cantilever-shaped, or otherwise shaped structure. In the latter case, the heating elements are supported by a diaphragm-shaped structure, for example.

Each of the belt-like heating elements consists of a resistive film of platinum or nickel and a heat-resistant insulating film that covers the resistive film. The resistive film exhibits excellent stability at high temperatures. As the operating temperature of the belt-like heating elements of the moisture-sensitive device is increased, higher sensitivity is obtained, because the difference between the output signals produced from moist air and dry air increases. The resistive film of platinum or nickel operates reliably within a high-temperature range of 300° to 400° C. The prior art device using thermistors can operate only up to about 200° C. In this way the novel device exhibits unparalleled response characteristics. Platinum is preferable to nickel, since platinum is more resistant to oxidation at high temperature.

The resistive film is formed to a thickness of 2000 to 5000 Å. If the film is thinner than 2000 Å, then it is impossible to bond lead wires to the film. If the film is thicker than 5000 Å, then it takes a long time to form and etch the film. In addition, the insulating film must be made thicker accordingly. This deteriorates the thermal insulation. The resistive film is patterned into a desired form so as to have a given resistance value. Thus, the belt-like heating elements are formed. As an example, a part of the resistive film is machined into a zigzag or meandering pattern either having a given width or consisting of parts spaced regularly from each other by micromachining techniques. In the case of a meandering pattern, making the width small is desirable, because a high resistance value is maintained. For instance, the width is 1 to 10 μm, preferably about 5 μm.

In this novel moisture-sensitive device, lead wires for supplying electric current are connected with the belt-like heating elements.

One of the belt-like heating elements is formed into a reference element, while the other is formed into a detector element. The heating element forming the reference element is hermetically sealed by a sealing cap coupled to the substrate, and isolated from the outside atmosphere. The inside of the cap constitutes a given moist atmosphere which can include dry condition. The belt-like heating element forming the detector element may be designed to be exposed to the outside atmosphere. This detector element may also be formed simply by exposing the belt-like heating element to the outside atmosphere. Preferably, a sealing cap is used for the reference element, and the cap is provided with holes that open into the outside atmosphere. In this case, the holes may be formed at any arbitrary positions. Where a multiplicity of moisture-sensitive devices are formed on a single wafer, water is used to cut the wafer into individual devices, or dice. In order to prevent the water from entering the cap, it is desired to form the holes at the junction of the substrate and the cap.

The belt-like heating elements can be formed and held on the substrate by micromachining techniques used in semiconductor fabrication processes such as thermal oxidation, sputtering, vapor deposition in vacuum, other film-forming techniques, and photolithography.

Micromachining techniques such as etching or photolithography can be directly applied to the fabrication of the sealing cap. The cap can be joined by screen printing, coating, sintering, or other process. These techniques are described in detail in the description of the examples of the invention.

Preferably, the belt-like reference element and the belt-like detector element are held on the same substrate by similar structures. It is desired that the two belt-like heating elements be hermetically sealed in an enclosure and that the heating elements be sealed by their respective casings within the enclosure. The casing sealing the detector element is provided with thin holes for communication with the outside atmosphere. As a result, both heating elements dissipate heat at substantially the same efficiency and show the same dependence of the moisture-sensitive characteristics upon temperature.

The novel moisture-sensitive device of the invention is designed so that the amount of water vapor contained in the detected atmosphere is measured from the difference between the outputs from the reference element and the detector element, utilizing the difference in resistance between both elements. As an example, a bridge circuit is built from the lead wires bonded to both heating elements. When the bridge circuit is not in balance, the output produced is used as the detector output. This is described in greater detail in the description of the examples of the invention.

In the moisture-sensitive device built as described thus far, the heating elements are heated by their respective resistive films made from platinum or nickel that are stable against heat. The amount $\phi$ of heat dissipated from the substrate is suppressed, because the recesses are formed in the substrate, and because the belt-like heating elements are supported by a bridge-, cantilever- or diaphragm-shaped structure. Therefore, the amount of heat dissipated depends upon the heat conduction coefficient of the atmosphere that is determined by the amount of water vapor contained in the atmosphere surrounding the heating element. Consequently, the change in the amount of heat dissipated by the heating elements reflects the change in the humidity of the surrounding atmosphere, and the changes in the resistance values of the resistive films. One of the heating elements is hermetically sealed within an atmosphere of a given humidity, while the other is exposed to the detected atmosphere. Hence, the difference between the outputs from the heating elements is not affected by the temperature of the atmosphere. The novel moisture-sensitive device has the following practical advantages.

(1) It is possible to directly detect the amount of water vapor. This detection of humidity is more advantageous than detection of relative humidities, especially where the temperature of the detected atmosphere changes rapidly.

(2) The heating elements are thermally insulated well, i.e., the heat capacity of the device is reduced to a minimum. Resistive films which have large temperature coefficients of resistance are used. Suitable resistive films are made from Pt or Ni which are chemically stable and resistant to heat. Therefore, the novel device can accomplish improved stability, higher sensitivity of water vapor detection higher response speed, and lower consumption of electrical power.

(3) Since it detects water vapor by physical means, it is stable against contamination of the surface of the device and so it has good environmental resistance.

(4) A batch of novel devices can be fabricated by ordinary semiconductor fabrication processes or their applied techniques. Therefore, the novel devices are excellent in reproducibility and compatibility, and are economical to fabricate.

(5) The novel moisture-sensitive device is suitably used as a sensor for detecting the completion of cooking of food in a microwave oven.

While the invention is now described in detail in its preferred examples, it is to be understood that the invention is not limited thereto.

Figure 1A:
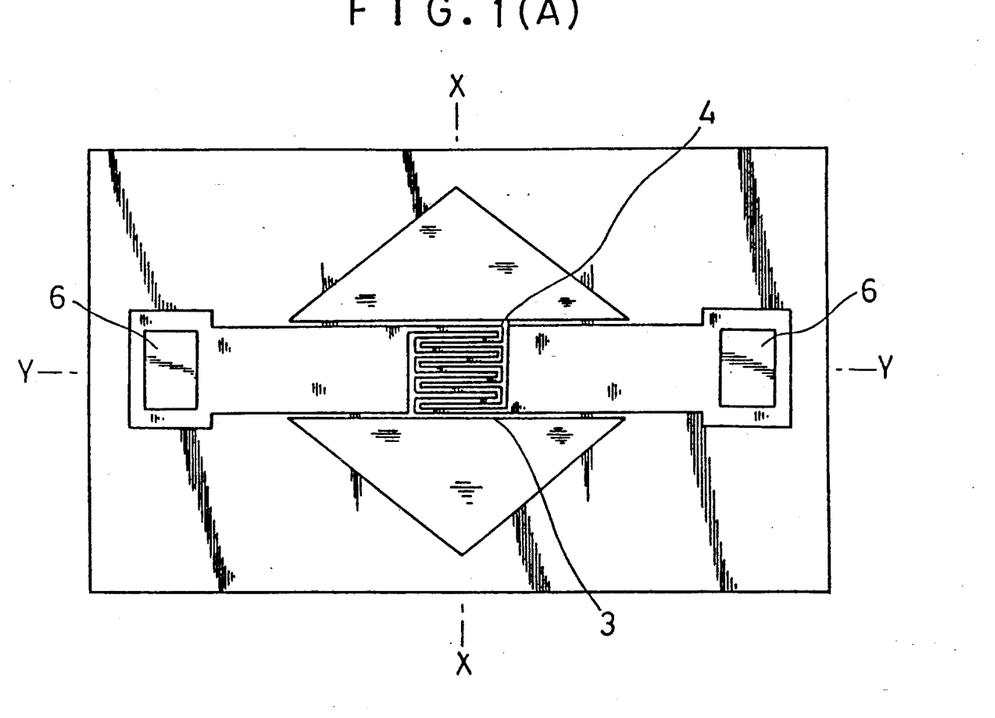
FIG. 1(A) is a schematic plan view of the structure of one example of the micro bridge type element for use on a moisture-sensitive device according to the invention.
Figure 1B:
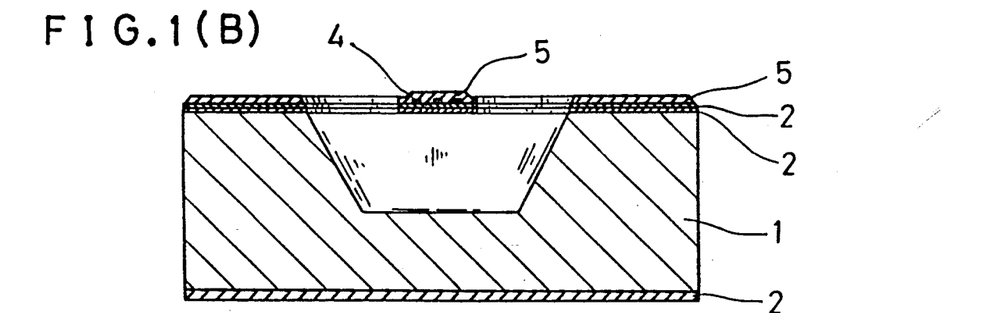
FIG. 1(B) is a cross-sectional view taken along line X—X of FIG. 1(A)
Figure 1C:
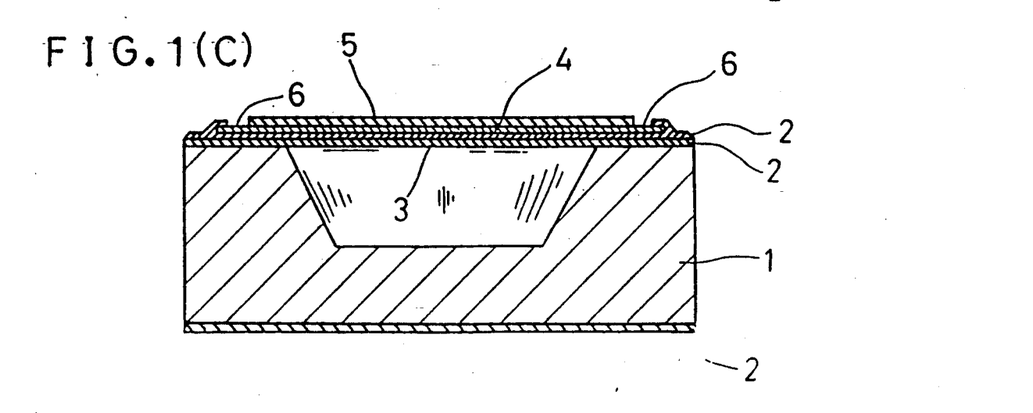
FIG. 1(C) is a cross-sectional view taken along line Y—Y of FIG. 1(A)

FIG. 1 shows a recess formed in a moisture-sensitive device according to the invention and a belt-like heating element disposed at the position of the opening of the recess. FIG. 1(A) is a schematic plan view of these portions of the device. FIG. 1(B) is a cross-sectional view taken along line X—X of FIG. 1(A). FIG. 1(C) is a cross-sectional view taken along line Y—Y of FIG. 1(A). An insulating layer 2 made of a thin film is formed on a substrate 1 of silicon. The layer 2 is shaped like a bridge. Then, the substrate 1 of silicon is etched anisotropically along the crystallographic axis to form a hollow structure between the substrate 1 and a micro bridge 3 formed from the insulating layer. Thus, the device is excellent in thermal insulation and has a small heat capacity. A resistive thin film 4 made from a sensor material is formed into a desired pattern on the micro bridge 3 so as to obtain a desired resistance value. A protective film 5 made from an insulating material is formed on the resistive film 4.

The process by which the device shown in FIG. 1 is fabricated is now described in detail. First, the thin insulating layer 2 of $SiO_2$, $Si_3N_4$, $Al_2O_3$, or other material is formed on the substrate 1 of silicon by thermal oxidation, sputtering, vapor evaporation in vacuum, or chemical vapor deposition, depending on the material. For the silicon substrate 1, the chemical etching rate differs with the orientation of crystallographic axis. The insulating layer 2 underlies the micro bridge 3. In this example, a film of $SiO_2$ is formed by thermal oxidation to prevent formation of etch pits when the silicon substrate is later etched. At the same time, $SiO_2$ is deposited on the rear surface and on the side surfaces of the substrate to form a mask that is used when the silicon substrate is later etched. In order for the resistive film to adhere well to the insulating layer, a film of $Al_2O_3$ is formed on the film of $SiO_2$ by sputtering or anodization to form the insulating layer 2 consisting of two films made from $Al_2O_3$ and $SiO_2$, respectively. The insulating layer 2 may also be a single film of $SiO_2$, $Si_3N_4$, or $Al_2O_3$, depending on the material of the resistive film or on the method by which the insulating film is formed. Considering the strength of the bridge, silicon can be left at a given thickness under the insulating layer underlying the micro bridge 3. The portion underlying the left silicon may be removed, and the bridge may be composed of two layers, i.e., the insulating layer and the layer of silicon that is the material of the substrate. In this case, the surface of the substrate over which the bridge is to be formed has been previously doped heavily with boron, or boron has been previously diffused into the surface at a high concentration. The portion treated in this way is used as a stopping layer when anisotropic or chemical etching is done. The result is that the bridge comprises the insulating layer and the layer of silicon doped with boron.

Figure 2:
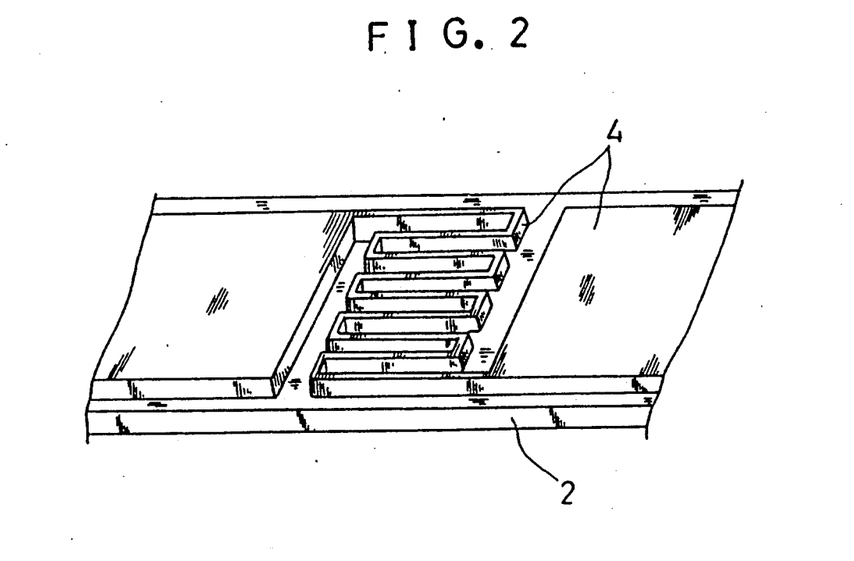
FIG. 2 is a perspective view of a patterned element for use on a moisture-sensitive device according to the invention.

Then, a metal such as platinum or nickel which has a large temperature coefficient of resistance is sputtered or deposited on the insulating layer 2 in a vacuum. The metal layer is formed into a desired pattern on the portion which forms the micro bridge 3 on the insulating layer when the silicon substrate is later etched. The patterning is conducted by photolithography and dry etching or chemical etching. The patterned metal layer forms the resistive film 4 having a desired resistance value. In this example, the resistive film 4 is made from platinum which is stable against chemicals and also against heat. The film 4 is formed into a zigzag or meandering pattern by dry etching as shown in FIG. 2. At this time, the platinum film has a thickness of 2000 to 5000 Å, typically 5000 Å. The meandering pattern has a width of 1 to 10 μm, typically 5 μm. Thereafter, the upper insulating layer 5 which serves as a protective film is formed on the resistive film 4 by sputtering, vapor deposition in vacuum, thermal oxidation, chemical vapor deposition, or other process. The insulating layer 5 acts as a mask when the silicon substrate is later etched. In this specific example, a film of $Al_2O_3$ which adheres well to platinum and exhibits good weatherproofness is formed by sputtering.

Subsequently, the portion of the silicon substrate which is located under the lower insulating layer 2 is selectively etched away to form the micro bridge 3 consisting of upper insulating layer 5, lower insulating layer 2, and resistive film 4. The upper and lower insulating layers are etched into a bridge pattern by photolithography, chemical etching, and dry etching to expose the silicon substrate located under the insulating layers. At the same time, the upper insulating layer is etched into a bonding pad with which lead wires extending to the platinum film are connected. More specifically, the film of $Al_2O_3$ is chemically etched, using a solution of phosphoric acid. The layer of $SiO_2$ is treated by chemical etching or dry etching, depending on the thickness of the film. After the upper film of $Al_2O_3$ of the pad is etched, the platinum resistive film is exposed. When the lower insulating layer of $Al_2O_3$ or $SiO_2$ is etched, the exposed film of platinum is resistant to the etchant and stable, whether the etching is chemical etching or dry etching. Therefore, the pad 6 can be created well. The exposed portions of the silicon substrate are chemically etched, using an alkaline solution of ethylenediamine pyrocatechol or KOH, so that the silicon crystal is anisotropically etched. As a result, the silicon substrate located under the insulating layer is etched into a bridge pattern to form the micro bridge 3 consisting of upper insulating layer 5, lower insulating layer 2, and resistive film 4. The upper and lower insulating layers can be films of $Si_3N_4$, which are similar in characteristic to the film of $Al_2O_3$. The upper and lower insulating layers are used as masks for the anisotropic etching. When the (111) plane of the (100) silicon substrate is exposed, the etching is performed.

Figure 3A:
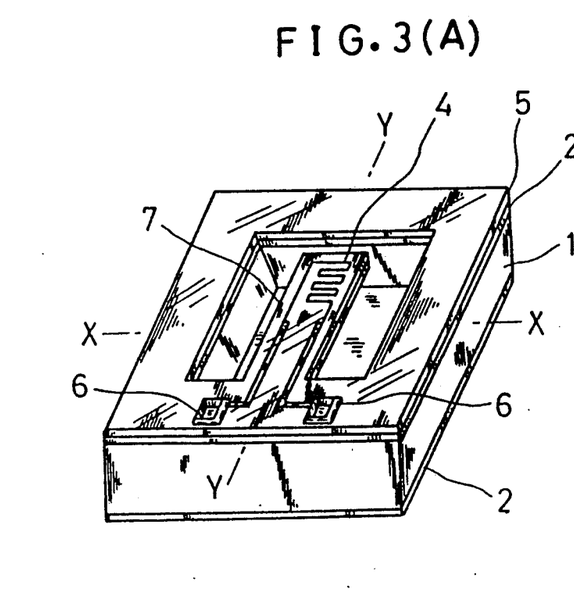
FIG. 3(A) is a perspective view of a cantilever type element for use on a moisture-sensitive device according to the invention.
Figure 3B:
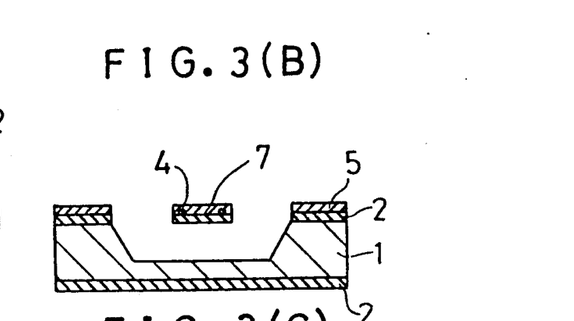
FIG. 3(B) is a cross-sectional view taken along line X—X of FIG. 3(A)
Figure 3C:
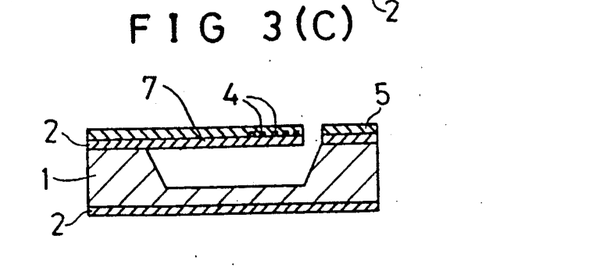
FIG. 3(C) is a cross-sectional view taken along line Y—Y of FIG. 3(A)

Another element for use on a moisture-sensitive device according to the invention is shown in FIG. 3. FIG. 3(A) is a perspective view of the element. FIG. 3(B) is a cross-sectional view taken on line X—X of FIG. 3(A). FIG. 3(C) is a cross-sectional view taken on line Y—Y of FIG. 3(A). This element has a resistive layer 4 on an insulating, cantilever-shaped layer 7 which is formed by patterning an upper insulating layer 5 and a lower insulating layer 2. This element is slightly inferior in mechanical strength to the above-described element but provides better thermal insulation.

The fundamental micro bridge type device and cantilever type device are formed by the processes described above. When the meandering pattern of the platinum resistive film is electrically energized and heats up to a certain temperature, the temperature changes according to changes in the amount of water vapor. This temperature change varies the resistance value. In this way, the amount of water vapor can be detected.

Figure 4A:
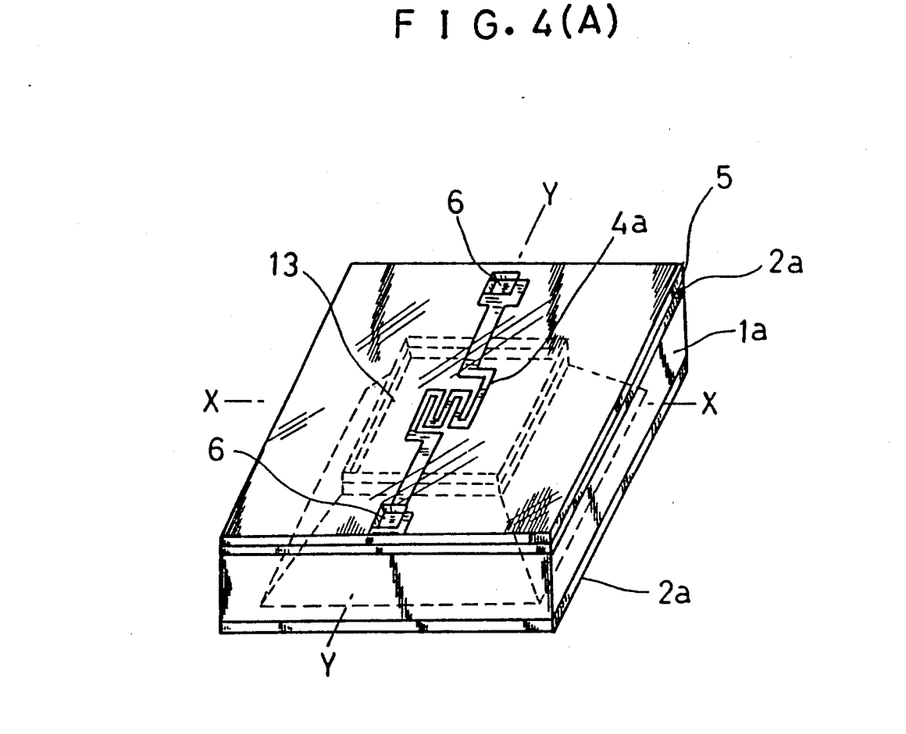
FIG. 4(A) is a perspective view of a diaphragm type element for use on a moisture-sensitive device according to the invention.
Figure 4B:
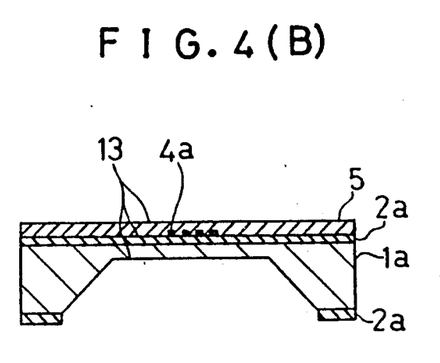
FIG. 4(B) is a cross-sectional view taken along line X—X of FIG. 4(A)
Figure 4C:
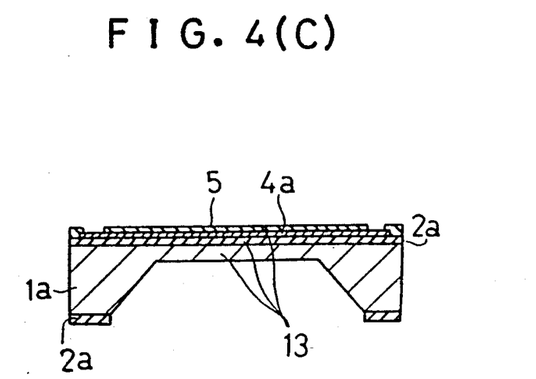
FIG. 4(C) is a cross-sectional view taken along line Y—Y of FIG. 4(A)

A further element for use on a moisture-sensitive device according to the invention is shown in FIG. 4. FIG. 4(A) is a perspective view of the element. FIG. 4(B) is a cross-sectional view taken on line X—X of FIG. 4(A). FIG. 4(C) is a cross-sectional view taken along line Y—Y of FIG. 4(A). An insulating thin film $2a$ is formed on the front surface, the rear surface, and the side surfaces of a silicon substrate $1a$. The insulating layer $2a$ on the rear surface of the silicon substrate $1a$ is etched into a desired form having desired dimensions according to the pattern needed to create a diaphragm. Thus, a mask for anisotropic etching is created. The anisotropic etching is started from the center of the rear surface of the silicon substrate $1a$ on which the insulating layer $2a$ is not formed. The central portion of the silicon substrate $1a$ is then thinned. A diaphragm 13 consisting of the thin insulating layer formed on the silicon substrate $1a$ and a layer of the silicon substrate material is formed. A resistive thin film $4a$ of nickel is formed on the diaphragm 13. The film $4a$ is formed into a desired form having specified dimensions, such as a meandering pattern similar to the pattern shown in FIG. 2. A protective film is formed on the resistive film. In this way, an element including the diaphragm 13 is fabricated.

The silicon substrate has been previously doped heavily with boron to form a stop layer in the silicon layer of the diaphragm 13. Therefore, the diaphragm comprises the silicon layer doped with boron and the insulating layer. It is not always necessary to control the thickness of the silicon layer by doping it with boron. It is also possible to control it by only controlling the time during which anisotropic etching is carried out. Further, this portion of the silicon layer may be fully etched away to form the diaphragm only from the insulating layer.

The thermal insulation of the resistive film of the diaphragm type moisture-sensitive element manufactured in this way is greatly superior to the thermal insulation of the resistive film of the prior art thermal conduction type moisture-sensitive element. That is, the novel element has a greatly reduced heat capacity. However, the diaphragm type, element is somewhat inferior in response characteristics compared to the bridge type and cantilever type elements. In spite of this fact, the diaphragm type element is superior to the bridge type and cantilever type elements, because the mechanical strength of the diaphragm is excellent. Accordingly, the diaphragm type element which has high sensitivity, high-speed response, and low consumption of electrical power can be advantageously used in an environment requiring high mechanical strength.

A moisture-sensitive device equipped with a pair of elements of the structure described above are next described. The elements are formed on a single substrate.

Figure 5A:
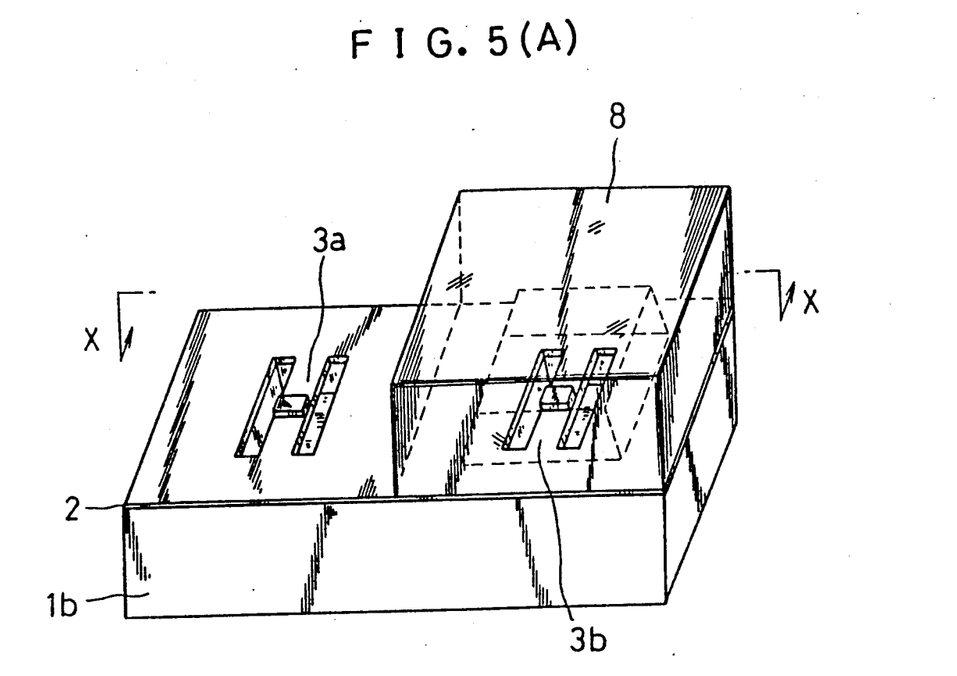
FIG. 5(A) is a perspective view of a moisture-sensitive device according to the invention.
Figure 5B:
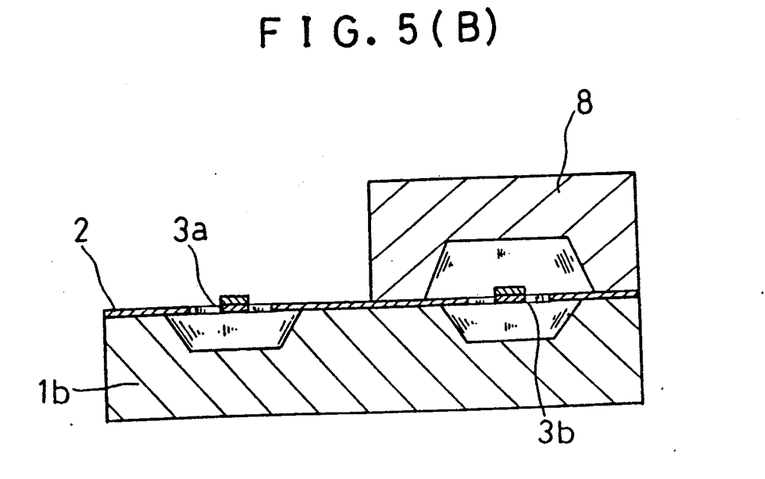
FIG. 5(B) is a cross-sectional view taken along the line X—X of FIG. 5(A)

FIG. 5 shows the structure of a moisture-sensitive device according to the invention. FIG. 5(A) is a perspective view of the device. FIG. 5(B) is a cross-sectional view taken on line X—X of FIG. 5(A). This devices includes a substrate $1b$ on which a pair of micro bridge elements having the same characteristics are formed. Each micro bridge element is the same as the micro bridge element shown in FIG. 1 and has a resistive film of platinum. One of the elements is a detector element $3a$, while the other is a reference element $3b$. A sealing cap (hereinafter referred to as the micro cap) is placed over the reference element $3b$ to isolate it from the outside atmosphere. The cap is bonded to the substrate with a low melting glass or adhesive. The cap that takes the form of a container is created by half etching a box-like silicon block to form its one side. The reference element $3b$ is hermetically sealed within the micro cap and so the reference element $3b$ is unaffected by variations in the humidity of the outside.

Figure 6:
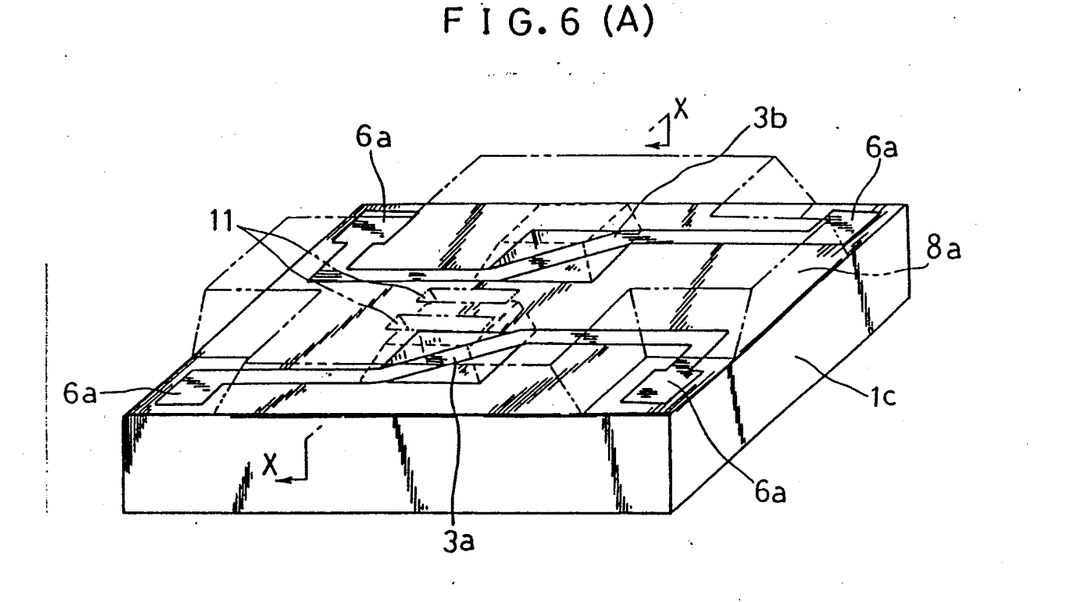
FIG. 6(A) is a perspective view of another moisture-sensitive device according to the invention.
FIG. 6(B) is a cross-sectional view taken along line X—X of FIG. 6(A)

FIG. 6 shows the structure of another moisture-sensitive device according to the invention. FIG. 6(A) is a perspective view of the device. FIG. 6(B) is a cross-sectional view taken on line X—X of FIG. 6(A). This device includes a substrate $1c$ on which a pair of micro bridge elements having the same characteristics are formed. Each micro bridge element has a resistive film of platinum and is the same as the micro bridge element shown in FIG. 1. One of the micro bridge elements is a detector element $3a$, whereas the other is a reference element $3b$. The elements $3a$ and $3b$ are hermetically sealed in a sealing micro cap $8a$ taking the form of, a container. The cap $8a$ is fabricated by anisotropically etching silicon. The detector element $3a$ is provided with minute holes 11 to permit water vapor to go into and out of the element. The reference element $3b$ is hermetically sealed as mentioned above to prevent water vapor from going into and out of the element.

Figure 7:
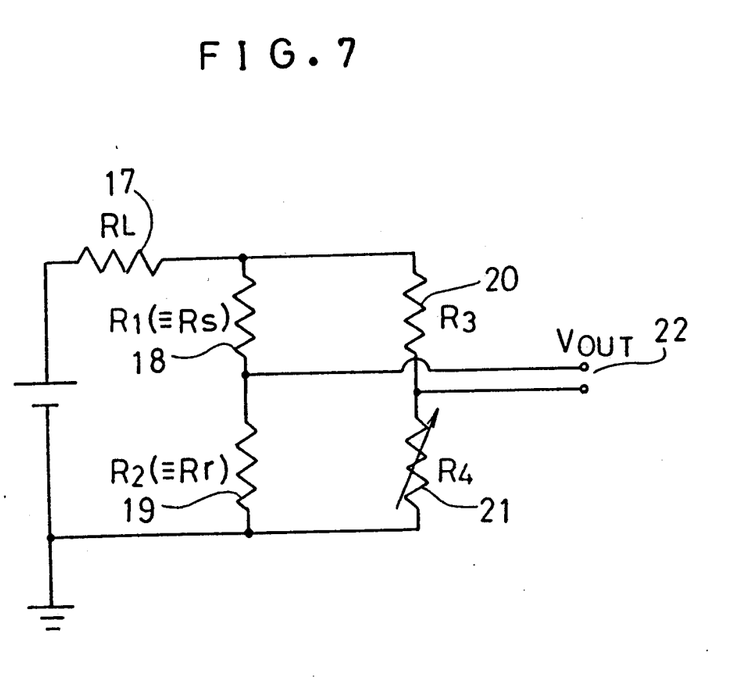
FIG. 7 is a diagram of a circuit for operation a moisture-sensitive device according to the invention.

A bridge circuit built as shown in FIG. 7 includes the resistive films of platinum of the elements $3a$ and $3b$ obtained in this way. The bridge circuit delivers an output signal $V_{OUT}$. The noise introduced in the output due to variations in the temperature of the atmosphere can be canceled out. Hence, an output signal reflecting only variations in the amount of water vapor is accurately derived. That is, the temperature dependence of the response to humidity can be compensated for, using the reference element $3b$.

The process by which the micro cap $8a$ is fabricated and the method by which the cap $8a$ is joined to the substrate $1c$ are next described in detail.

A film of $SiO_2$ is formed over the whole surface of a substrate of silicon by thermal oxidation. Then, the film of $SiO_2$ is etched into a desired pattern on both sides of the substrate by photolithography and chemical etching or dry etching. At this time, two recesses 9 and 10 are farmed in the micro cap, together with and the minute holes 11 permitting water vapor to go into and out of the element $3a$. Then, the exposed portions of silicon are anisotropically etched, using an alkaline solution of ethylenediamine pyrocatechol or KOH, in the same way as the elements of the body. Thus, the micro cap 8 is obtained. Finally, the micro cap is joined to the elements of the body to manufacture the moisture-sensitive device shown in FIG. 6. More specifically, a low melting glass or other cement 12 is employed to join them together. The low-melting glass 12 is patterned on the joint portions of the micro cap by screen printing, coating, or other method. Then, the cap is caused to register with the elements of the body. The assembly is sintered inside a furnace which contains an atmosphere of an extremely low humidity, to join the cap to the elements. The elements to which the micro cap has been joined are mounted on an ordinary or known TO-5 package. Wire leads are bonded to the pad $6a$, thus completing the device. A process for manufacturing a single device has been described thus far. In practice, two wafers and corresponding elements, and micro caps are simultaneously fabricated until the joining step is completed. After the joining step, the two wafers are separated by dicing to produce separate devices. Consequently, productivity is enhanced, and the cost of manufacture is reduced.

Changes in the amount of water vapor can be accurately detected, employing this moisture-sensitive device and the bridge circuit shown in FIG. 7. The operation is now described. The resistive film $[R_1 (\equiv R_s)]$ 18 of platinum of the detector element is connected in series with the resistive film $[R_2(\equiv R_r)]$ 19 of platinum of the reference element. These resistive film are electrically energized so that they may be heated to about 300° C. At this time, a current-limiting resistor $(R_1)$ 17 is added to provide over-current protection. Adequate fixed resistors are connected with $R_3$ 20 and $R_4$ 21. Then, an adjustment is made so that the output $V_{OUT}$ 22 obtained before measurement equals a reference level. Therefore, it is desired to use a variable resistor as $R_4$ 21. Under this condition, if the amount of water vapor contained in the atmosphere varies, then the resistive film 18 of platinum of the detector element is affected by the variation and the temperature of the element changes. Thus, only the resistance value of the detector element varies, unbalancing the bridge circuit. As a result, a voltage corresponding to the amount of water vapor is obtained at the output $V_{OUT}$ 22 If the temperature of the atmosphere changes, the temperature of the two elements change by the same amount, and their resistance values change by the same amount. The output a $V_{OUT}$ 22 is maintained at the reference level and does not vary. In this way, the temperature dependence of the device's response to the humidity is considerably compensated for. This enables accurate detection. The output signal from the novel device is superior in signal-to-noise ratio to the output from the prior art sealed package type device.

Figure 8A:
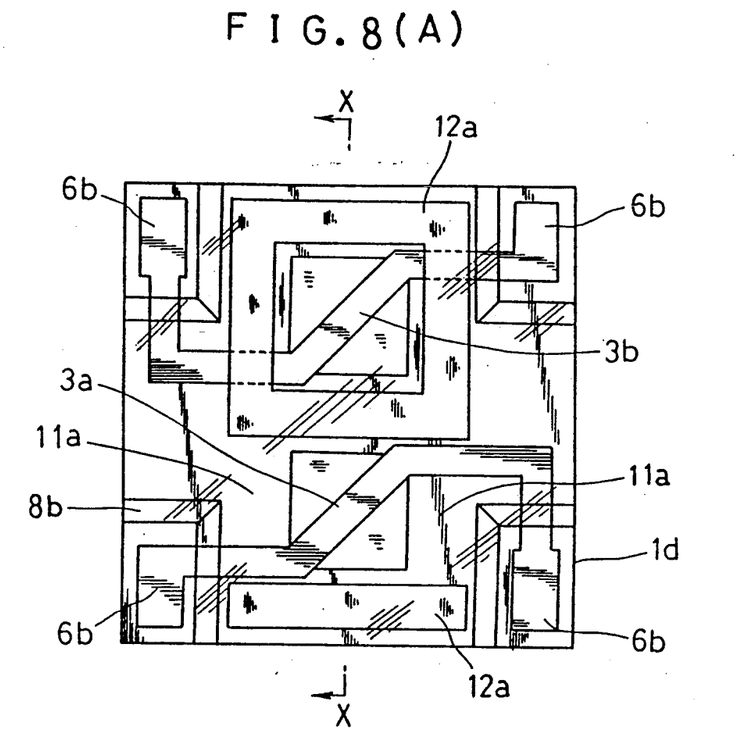
FIG. 8(A) is a plan view of a further moisture-sensitive device according to the invention.
Figure 8B:
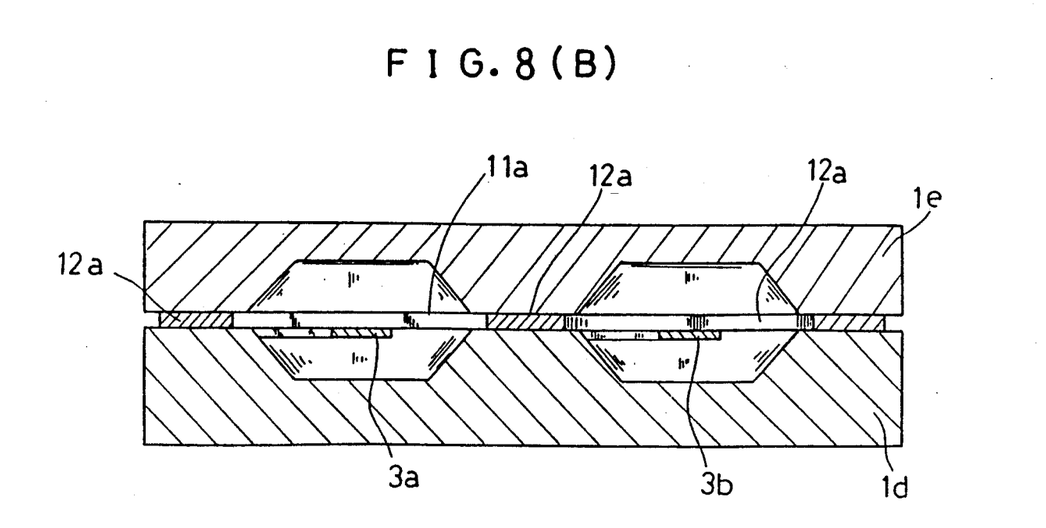
FIG. 8(B) is a cross-sectional view taken along line X—X of FIG. 8(A)

FIG. 8 shows a still another moisture-sensitive device according to the invention. FIG. 8(A) is a plan view of the device. FIG. 8(B) is a cross-sectional view taken along line X—X of FIG. 8(A). This moisture-sensitive device includes a substrate $1d$ and a pair of micro bridge elements of the construction shown in FIG. 1. The elements are formed on the substrate $1d$ and have the same characteristics. Each micro bridge element has a resistive film of platinum. One of the elements is a detector element $3a$, while the other is a reference element $3b$. A micro cap $8b$ is provided with recesses corresponding to the position of the substrate 1d. Also, the cap 8b is formed with cutouts for exposing the bonding pads 6b of the elements 3a and 3b. The recesses form spaces for the elements. Low-melting glass paste 12a for joining the cap to the substrate is applied to the micro cap 8b by screen printing in a pattern indicated by the hatching in FIG. 8(A). The paste is provisionally sintered to evaporate the solvent contained in the paste. Then, the substrate 1d and the micro cap 8b are placed in an opposite relation to each other within an atmosphere of dry air or air of a known humidity sealed in the space of the reference element 3b. The substrate 1d and the micro cap 8b are so arranged that their recesses together form spaces surrounding the elements 3a and 3b, respectively. Subsequently, heat is applied to melt the low-melting glass, to join the cap to the substrate. As a result, the space around the reference element 3b is isolated from the outside atmosphere and kept in a certain atmosphere. It is not always necessary that the sealed atmosphere be at the atmospheric pressure. At the same time, a space is formed around the detector element 3a. The gaps in the joined portions create vent holes 11a which are opposite to each other.

A plurality of moisture-sensitive, devices of the construction described above are batched on a silicon substrate and then they are separated by dicing.

During the above process, it is unlikely that cutting water for dicing will flow in from the vent holes and destroy the detector element 3a. If the cutting water should enter the space around the detector element 3a, then the water could be easily discharged, using at least two vent holes 11a disposed opposite to each other in the space. Also, it would be easy to clean and dry the space.

Each chip, or moisture-sensitive device, separated as described above is mounted on an electronic part stem. Wires are bonded to the pads 6b. Then, a mesh cap is placed on the chip to complete the moisture-sensitive device.

In the operation of the moisture-sensitive device as described above, electrical energy is supplied to the elements so that they may heat themselves. Heat is dissipated at rates corresponding to the amounts of water vapor contained in the spaces around the reference element and the detector element, respectively, i.e., at thermal conductivities of the spaces at their respective absolute humidities ($g/m^3$). Both elements are kept at a certain temperature and have given resistive values. The difference is detected as the output from the unbalanced bridge circuit. In this manner, the absolute humidity can be measured.

COMPARATIVE EXAMPLE

Figure 10:
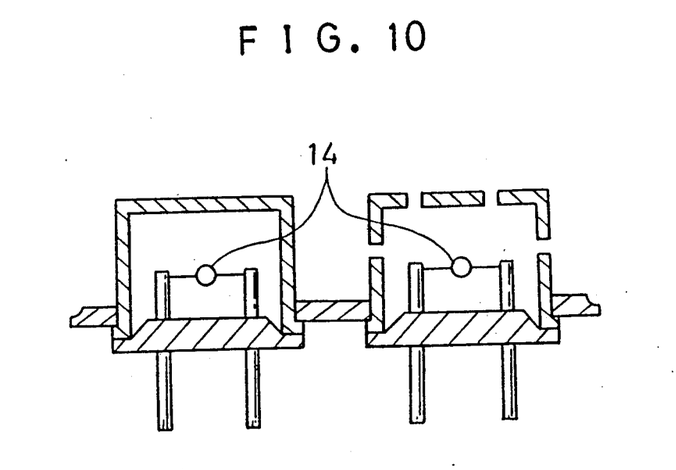
FIG. 10 is a schematic of a moisture-sensitive device using known bead-type thermistors.
Figure 11:
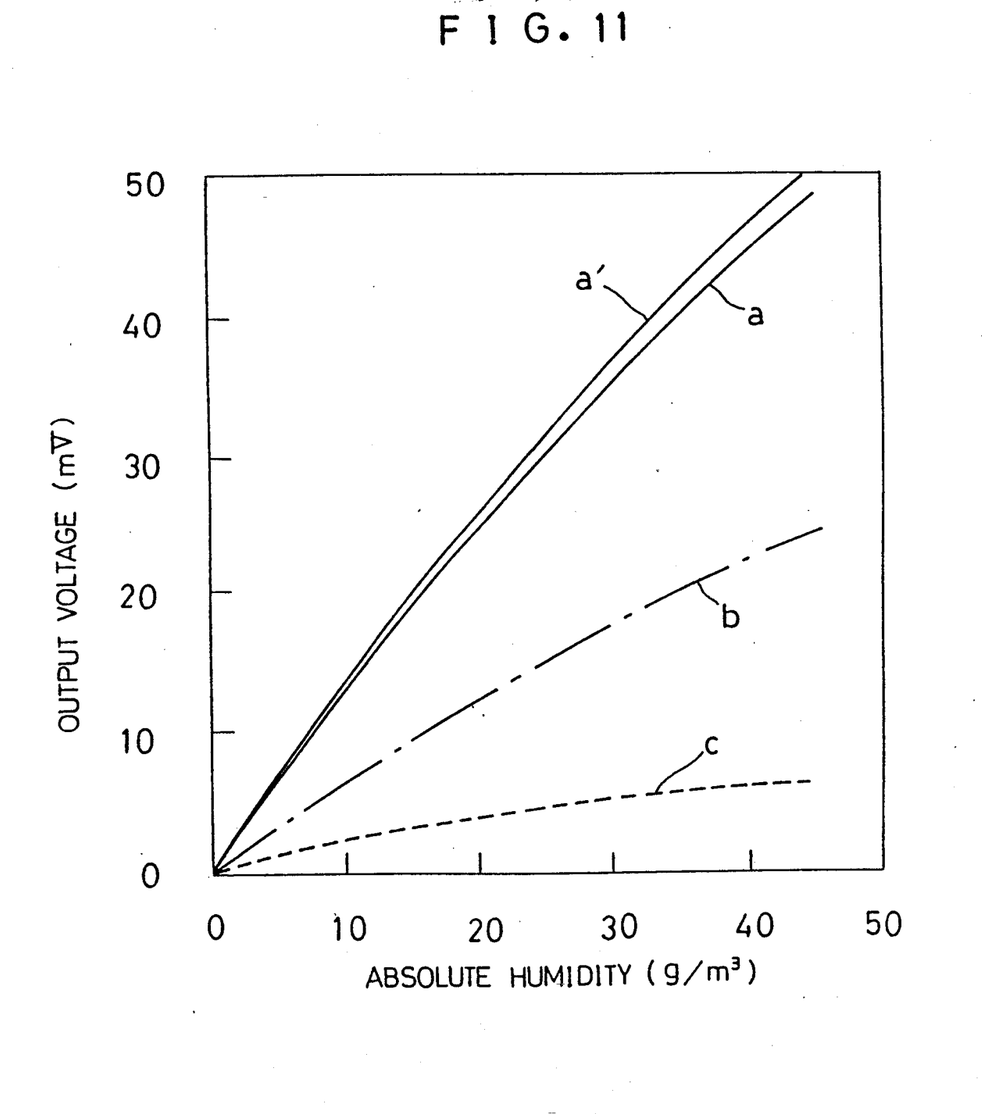
FIG. 11 is a graph comparing the sensitivity of a moisture-sensitive device according to the invention with the sensitivity of a conventional moisture-sensitive device.

FIG. 11 shows the output voltages from four devices at the same humidity. The temperature of the atmosphere surrounding the devices was 40° C. The absolute humidity was varied. The known bridge circuit shown in FIG. 7 was used. The four devices were a micro bridge type device (a) using resistive films of platinum according to the invention, another micro bridge type device (a') using resistive films of nickel, a further micro bridge type device (b) (FIG. 9) having resistive thin films made from thermistor material 15, and a device (c) (FIG. 10) using two bead-type thermistors 14. The sensitivities of the devices (a) and (a') according to the invention are twice as high as the sensitivity of the conventional device (b) and eight times as high as the sensitivity of the conventional device (c). The devices (a) and (a') were operated at temperatures of about 300° C. The device (b) was operated at about 150° C. The device (c) was operated at approximately 200° C. At these temperatures, the device operated reliably as described later.

Figure 12A:
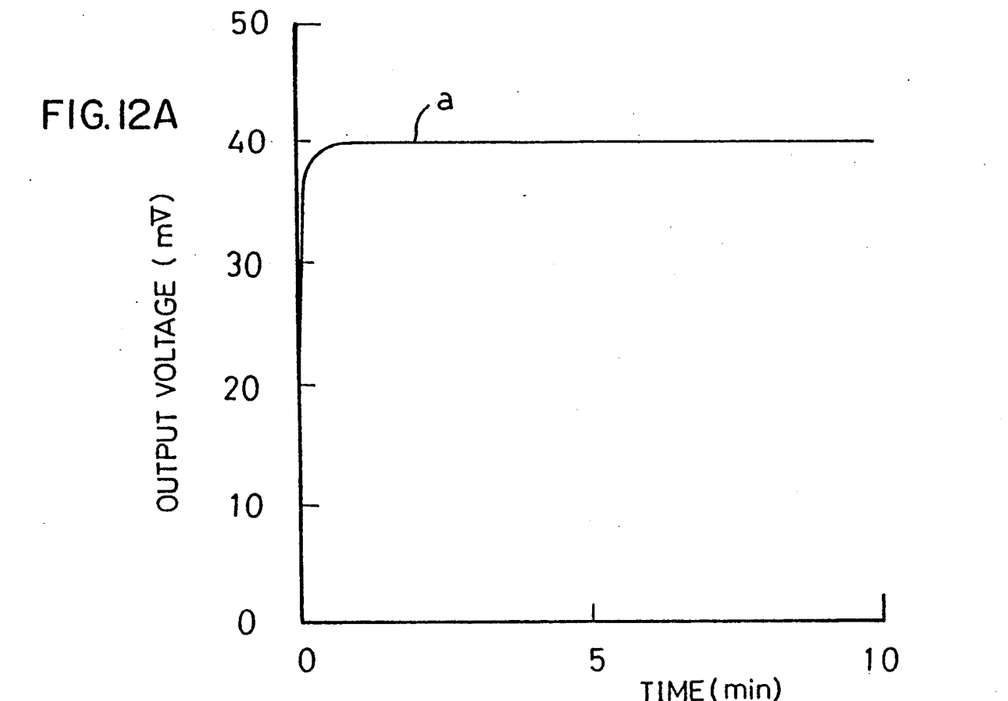
FIG. 12 shows graphs for comparing the speed of response of a moisture-sensitive device according to the invention with the speed of response of a conventional moisture-sensitive device.
Figure 12B:
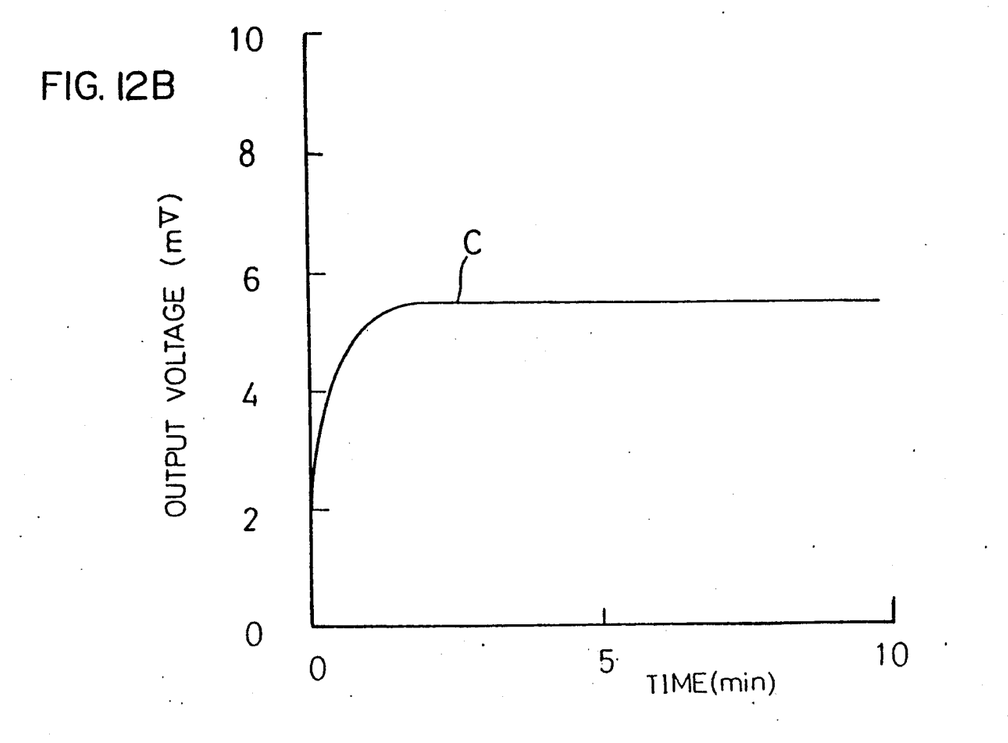

The speeds of response to moisture of the devices (a) and (c) are compared in FIG. 12. The circuits used and the operating temperatures were the same as those used in the above-described experiments on sensitivities (FIG. 11). The response characteristics of the circuits obtained when the humidity of the atmosphere was changed rapidly from 10 $g/m^3$ to 35 $g/m^3$ at a temperature 40° C. are shown. The response time of the novel device (a) was about 5 sec, while the response time of the conventional device (c) was about 50 sec. In this way, the response time of device (a) according to the invention is about ten times as higher than as the response time of the conventional device (c). The device (c) consumed electric power on the order of hundreds of milliwatts,, whereas the device (a) consumed electric power on the order of tens of milliwatts. In this way, the invention achieves a great reduction in the consumption of electric power.

Figure 13:
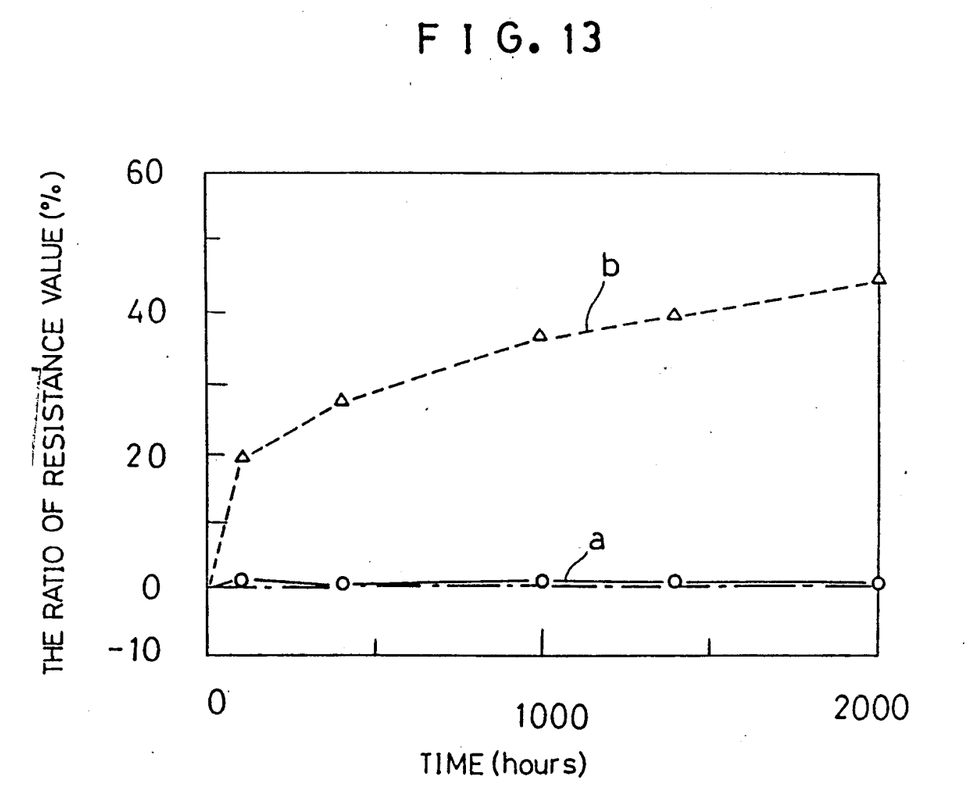
FIG. 13 is a graph comparing the stability of a moisture-sensitive device according to the invention with the stability of a conventional moisture-sensitive device.

The stability at high temperatures of the platinum resistive film was compared with the stability at high temperatures of the thin thermistor film, to check their reliability. The devices (a) and (b) were electrically energized at room temperature, so that they were heated to about 400° C. and 200° C., respectively. Then, they were allowed to stand. The ratio of the resistance value $R_0$ at an evaluating temperature of 0° C. to its initial value was measured. The ratios of the devices changed with time as shown in FIG. 13. For the device (b) having the thin film of a thermistor, the ratio increased at high rates. For the novel device (a) having the platinum resistive film, the ratio was quite stable. Hence, the device (a) is highly reliable.

As described thus far, the inventive moisture-sensitive device having platinum resistive films on a micro bridge-, cantilever-, or diaphragm-shaped insulating layer operates stably over a long period of time consumes much less electric power than the prior art device, responds at a high speed, and exhibits high sensitivity.

What we claimed is:

1. A moisture-sensitive device comprising:
   a substrate provided with a pair of recesses;
   a pair of belt-like heating elements extending over the recesses and formed adjacent at least one side of openings of the recesses, each of said heating elements comprising a resistive film of platinum or nickel and a heat-resistant insulating film covering the resistive film;
   an insulator formed between the substrate and the heating elements;
   a container, the inside of which is an atmosphere of a given humidity, the container being formed integral with the substrate and acting to isolate one of the heating elements from an outside atmosphere; and
   lead wires for supplying electric current to the heating elements.

2. A moisture-sensitive device of claim 1, wherein the resistive film has a thickness of 2000 to 5000 A.

3. A moisture-sensitive device of claim 1, wherein the resistive film is in a pattern form.

4. A moisture-sensitive device of claim 3, wherein the pattern form is a meandering pattern form.

5. A moisture-sensitive device of claim 1, wherein the belt-like heating element operates in the range of 300° C. to 400° C.

6. A moisture-sensitive device of claim 1, wherein the substrate is a silicon substrate.

7. A moisture-sensitive device of claim 1, wherein each of the belt-like heating elements has a container which is integral with the substrate and isolated from the outside atmosphere, the inside of one of the containers of the heating elements being an atmosphere of a given humidity, the other being provided with holes communicating with the outside atmosphere.

8. A moisture-sensitive device of claim 7 wherein the holes are formed at positions at which the containers are joined to the substrate.

9. A moisture-sensitive device of claim 7 wherein the substrate is a silicon substrate.

10. The moisture-sensitive device of claim 1, wherein said pair of belt-like heating elements are formed on opposite sides of openings of said recesses.

11. The moisture-sensitive device of plain 1, wherein said pair of belt-like heating elements are formed on the same side of openings of said recesses.

* * * * *